United States Patent [19]

Ballard

[11] Patent Number: 5,417,232
[45] Date of Patent: May 23, 1995

[54] MULTIPLE LOCK DENTAL FLOSS HOLDER AND SPOOL ENCLOSURE ASSEMBLY THEREFOR

[76] Inventor: Larry N. Ballard, 103 S. Kensington, LaGrange, Ill. 60525-2214

[21] Appl. No.: 124,972

[22] Filed: Sep. 21, 1993

Related U.S. Application Data

[63] Continuation-in-part of Ser. No. 951,452, Sep. 25, 1992, Pat. No. 5,301,698.

[51] Int. Cl.⁶ ............................................. A61C 15/00
[52] U.S. Cl. ..................................... 132/325; 132/326
[58] Field of Search ............... 132/323, 324, 325, 326, 132/327; 242/136, 137.1, 138, 137

[56] References Cited

U.S. PATENT DOCUMENTS

| | | | |
|---|---|---|---|
| 1,454,429 | 5/1923 | Dresser | 242/138 |
| 1,456,279 | 4/1923 | Patterson . | |
| 1,700,550 | 1/1929 | Stafford . | |
| 3,698,546 | 10/1972 | Kass | 242/137 X |
| 3,815,843 | 6/1974 | Fortune | 242/137.1 X |
| 3,861,406 | 1/1975 | Stitt . | |
| 3,871,393 | 3/1975 | Wharton . | |
| 3,924,647 | 12/1975 | Lindblad . | |
| 4,009,845 | 3/1977 | Santucci et al. | 242/137.1 X |
| 4,089,486 | 5/1978 | Carter | 242/137.1 X |
| 4,141,519 | 2/1979 | Tarrson et al. . | |
| 4,200,249 | 4/1980 | Syastelien et al. | 242/137.1 X |
| 4,254,786 | 3/1981 | Won . | |
| 4,729,392 | 3/1988 | Tenny . | |
| 4,901,742 | 2/1990 | Olson . | |
| 5,038,806 | 8/1991 | Ewald . | |
| 5,085,236 | 2/1992 | Odneal et al. . | |
| 5,261,625 | 11/1993 | Lanoue | 242/137.1 X |

Primary Examiner—Nicholas D. Lucchesi
Attorney, Agent, or Firm—James P. Hanrath

[57] ABSTRACT

A multiple lock dental floss holder comprises a body cooperative with a spool enclosure assembly to achieve multiple locking of a operative length of dental floss. An intermediate portion of the body of the dental floss holder has a through bore opening on one side to a spool receiving cavity and on the other side to an irregular surface. A spool enclosure piece or base is received into the spool receiving cavity and has an annular cavity between an annular flange skirt and a central hub or base for receiving a spool of dental floss. The central hub or a pin extends through the through bore of the intermediate portion and connects to a cap or cooperates with a pin base also having an irregular surface that is complimentary with the irregular surface of the intermediate portion to selectively achieve a mating or non-mating engagement therewith to selectively allow release or capture of a length of dental floss between the irregular surfaces. The floss enclosing piece or base, or a pin or an end cap are capable of being depressed by the fingers of a user to apply selective pressure against a length of dental floss. Further, the annular skirt of the spool enclosing piece or base has a plurality of guide teeth on its external surface cooperative with a ratcheting mechanism in the spool receiving cavity of the intermediate portion to allow rotation of the spool enclosure piece in only one direction.

38 Claims, 9 Drawing Sheets

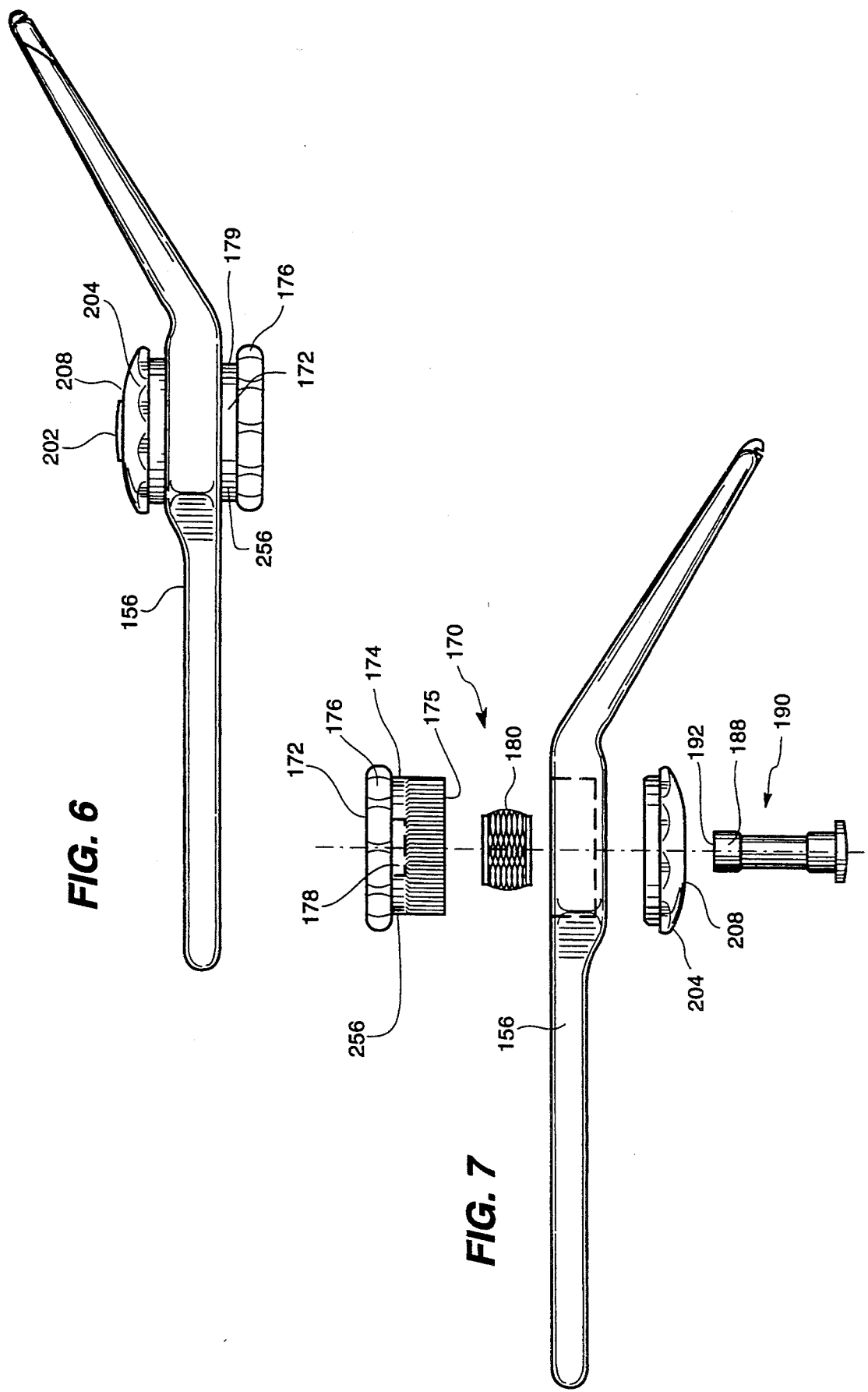

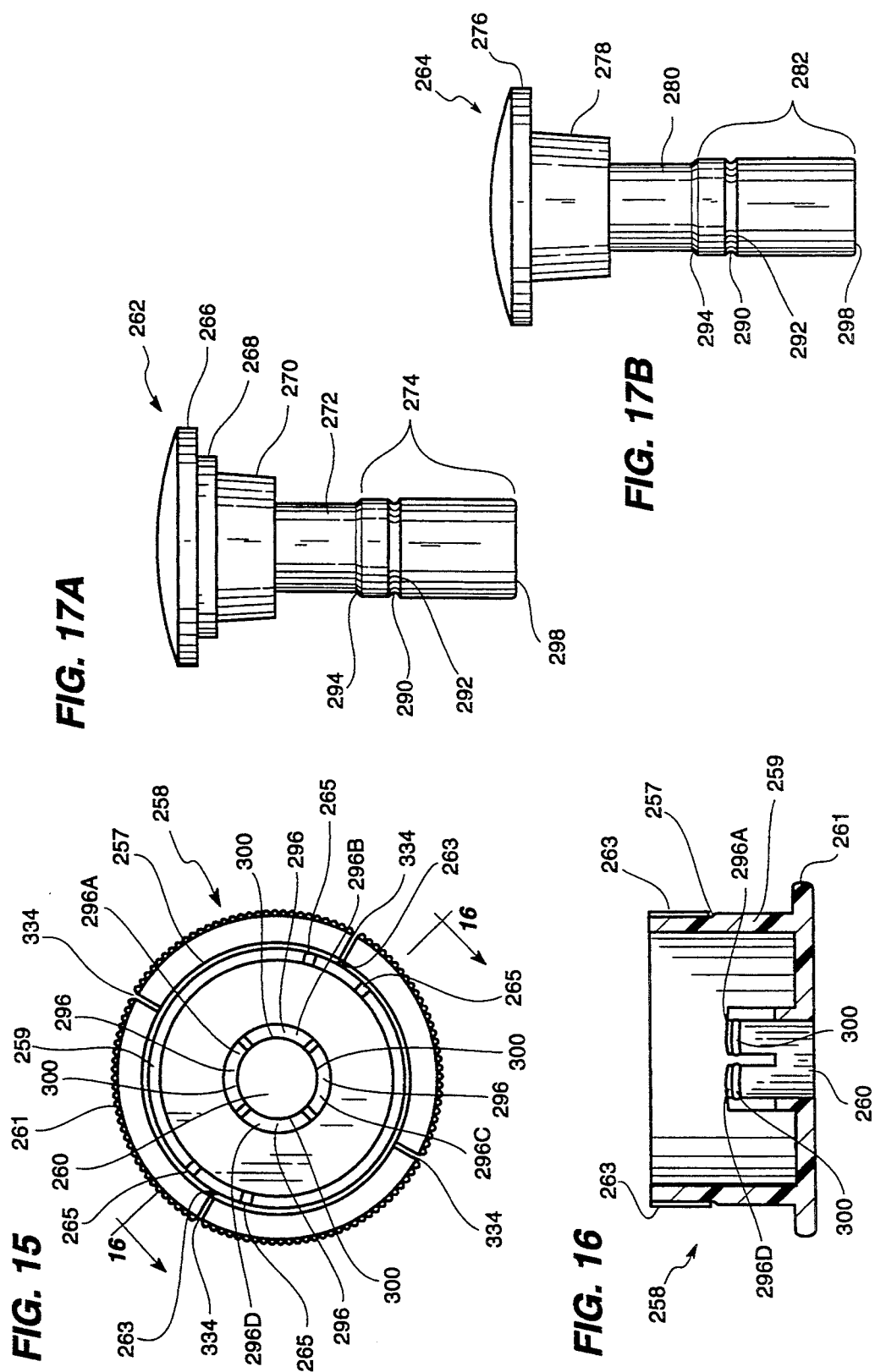

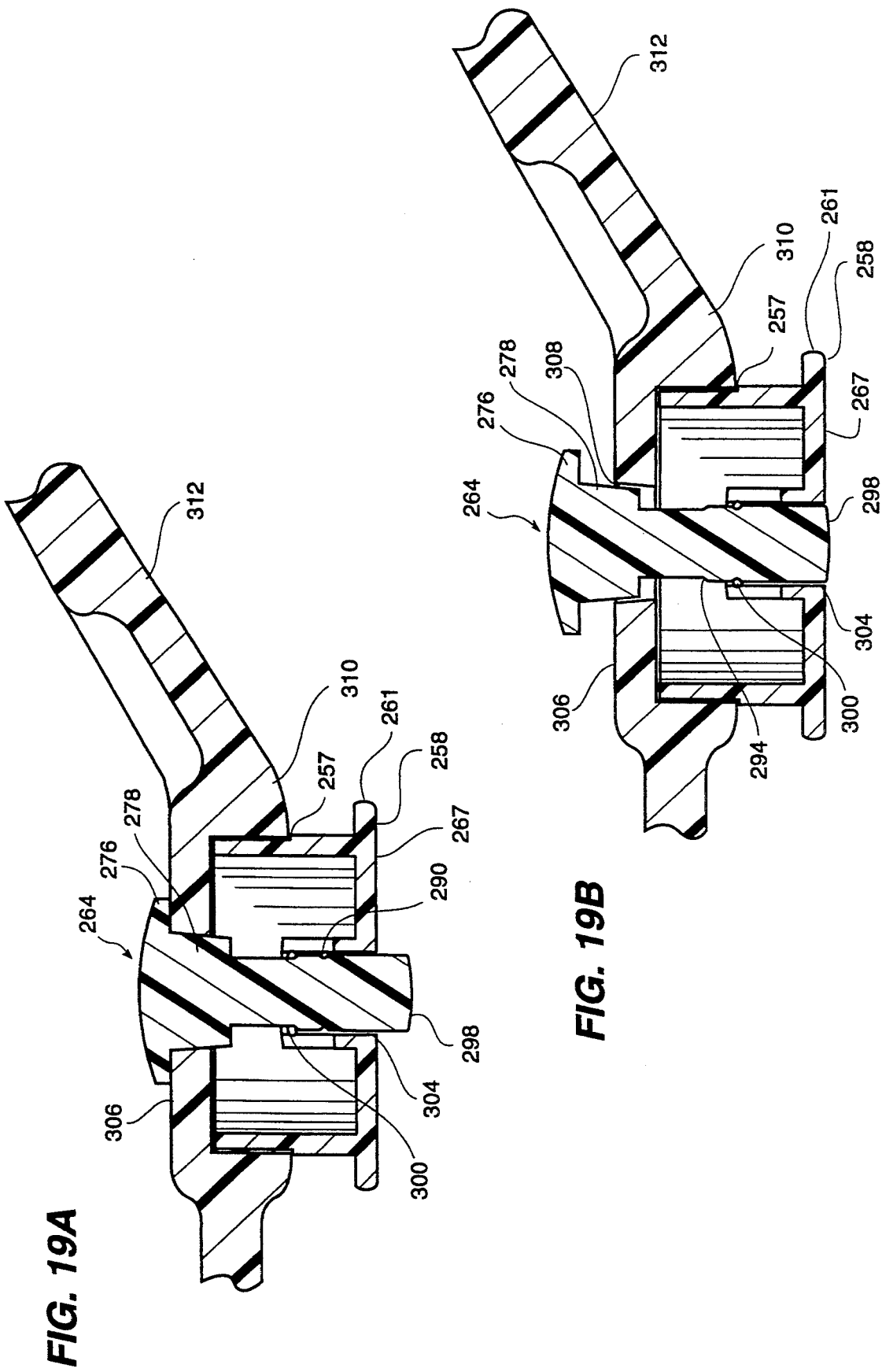

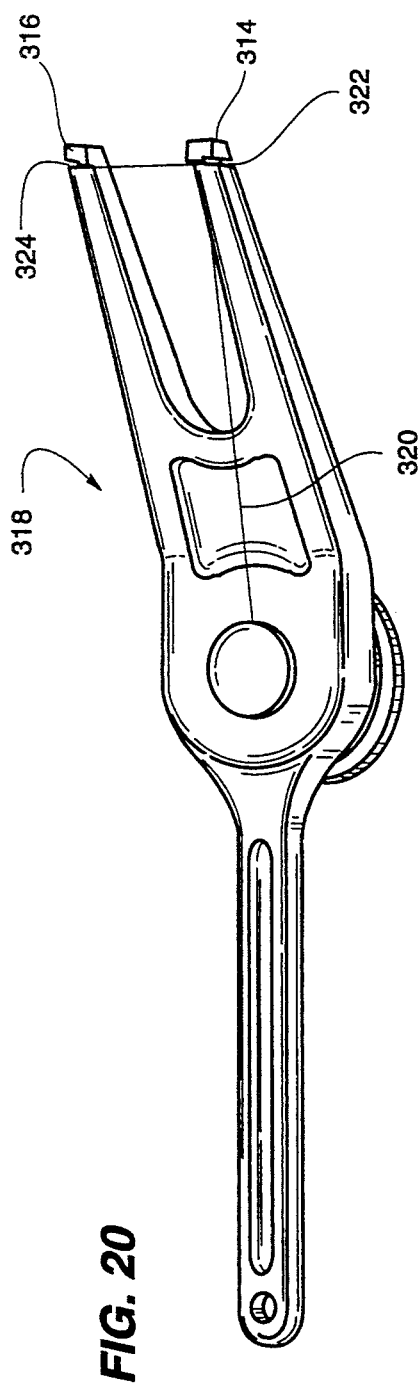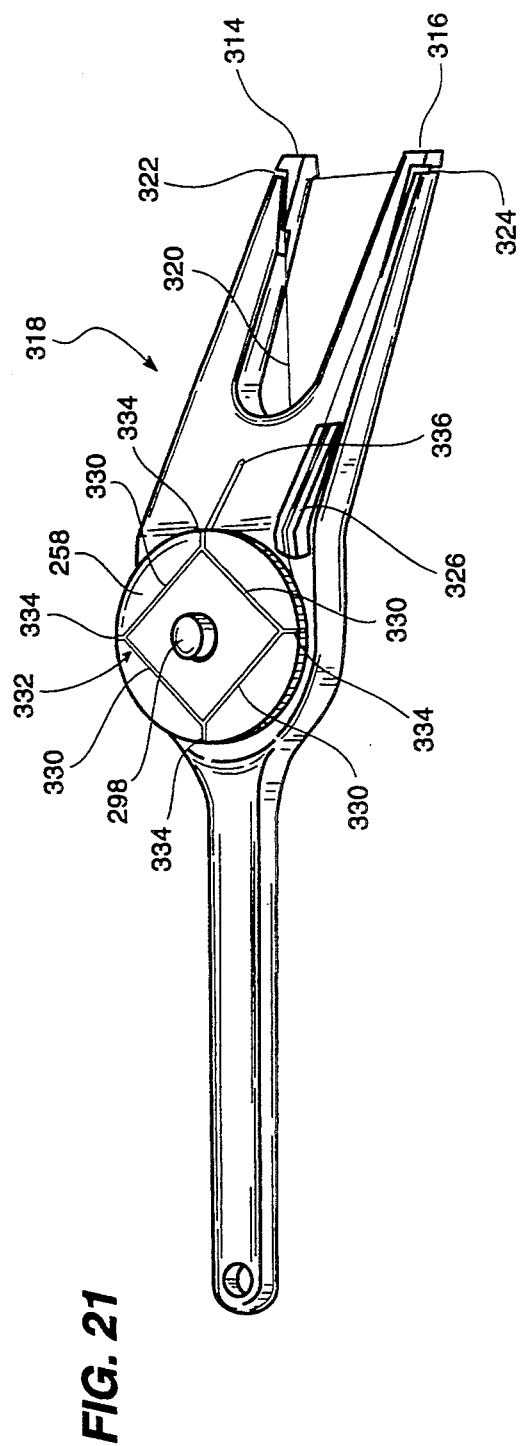

MULTIPLE LOCK DENTAL FLOSS HOLDER AND SPOOL ENCLOSURE ASSEMBLY THEREFOR

CROSS-REFERENCE TO RELATED APPLICATION

This application is a Continuation-in-Part of U.S. patent Ser. No. 07/951,452, filed Sep. 25, 1992 for MULTIPLE LOCK DENTAL FLOSS HOLDER AND SPOOL ENCLOSURE ASSEMBLY THEREFOR, now U.S. Pat. No. 5,301,698.

BACKGROUND OF THE INVENTION

1. Field of the Invention

The present invention relates generally to the field of oral hygiene, and more particularly to a MULTIPLE LOCK DENTAL FLOSS HOLDER AND SPOOL ENCLOSURE ASSEMBLY THEREFOR for receiving a spool of dental floss and dispensing and retaining a length of the dental floss in a taut condition.

2. Description of the Related Art Including Information Disclosed Under 37 CFR § 1.97-1.99

The dental profession has long recognized the benefits of regular use of dental floss in home dental care and oral hygiene programs. Heretofore, people have either chosen one of many dental floss holding devices that have been previously known, or they hold and maneuver dental floss with their fingers. The later procedure often involves wrapping the dental floss around the fingers, sometimes resulting in pain as flossing proceeds; the method of holding and manipulating dental floss with the fingers is also wasteful of flossing material, and is somewhat difficult, the degree of difficulty in part depending upon the relative size of fingers and mouth, dexterity, and patience.

Various dental floss holders have been developed to facilitate holding and tensioning the dental floss, and to facilitate the urging of dental floss between the teeth. Although in the prior art some dental floss holders are of disposable design, reusable dental floss holders utilizing commonly available dental floss are more often cost effective. Of the currently more popular reusable dental floss holders which are of low-cost construction, and which use widely available dental floss, most have a pair of spaced arms at the end of a supporting handle. A length of dental floss is strung between the ends of the spaced arms which have floss-receiving notches at their terminal ends. The ends of the dental floss are secured in some fashion or another, generally either by winding around a button or protrusion on the handle, or pulling the ends of the dental floss into inwardly tapered notches of frictional securing slots on the handle. These dental floss holders have only limited success commercially for a number of reasons, often including inadequate securing and/or tensioning of the dental floss and/or a design not easily maneuvered in the back of the mouth, and/or a design wasteful of dental floss, and/or a design with too much bulk and discomfort in use. Further, some prior art dental floss holders which use commonly available dental floss material require tie-down, knotting, loop-making, or other special treatment of one or both of the dental floss ends.

Additionally, many prior art dental floss holders do not fit commonly available toothbrush holders or cannot be hung from a hook which results in the device being stored out of site in for example, a medicine cabinet or a drawer or closet. Experience has shown that if the device is not conveniently displayed in full sight, it is not used on a regular basis and dental hygiene suffers.

In the present invention, there is disclosed a dental floss holder for receiving a spool of dental floss and dispensing and retaining a length of the dental floss in a taut condition by multiple means for maintaining tautness of the dental floss and a spool enclosure assembly therefor.

In U.S. Pat. No. 4,901,745 to Olson there is disclosed a dental flosser-dispenser which includes a pistol-grip shaped handle portion and a bow portion extending therefrom for holding a length of tension of floss between its tip and an anchoring mechanism. A spool of dental floss is provided in the handle and includes a detente system for selectively paying out new floss from the spool and anchoring the spool in place while the device is being used for flossing. An alternative embodiment of this dental floss dispenser may include a pistol-grip shaped handle portion in an elongate neck portion supporting a U-shape armature. The detente means for selectively permitting the floss to be unwound from the spool supported in the handle portion. Specifically, the handle portion includes housing halves that are fastened together whereby a hub member receives a spool of floss positioned over the hub and a screw having a finger-grip is accessible from the outside of the housing for tightening and loosening the flossing spool.

In U.S. Pat. No. 4,729,392 to Tenny there is disclosed an improved dental floss holder having a comparatively inflexible elongate member supporting two flexible spaced arms at opposite ends, and supporting an inflexible spaced arm between. A single length of dental floss is fastened near the terminal end of either flexible arm, then wrapped around the inflexible spaced arm, then fastened at the flexible spaced arm at the opposite end. This provides two taut and useable lengths of dental floss, either of which may be used for flossing while the other end of the dental floss holder is used as a handle. This dental floss holder utilizes buttons/protrusions in combination with frictional securing slots to thereby obtain two taut and useable lengths of dental floss in tandem when the dental floss holder has been strung for use.

In U.S. Pat. No. 4,141,519 to Tarrson et al there is disclosed a spool of thread, such as dental floss, which is housed in a holder. The thread or floss is wound on a bobbin having a hollow, cylindrical hub area. A crutch for controlling the bobbin rotation comprises a split post having an enlarged cross section near the center thereof. This split post fits into the hollow cylindrical hub area of the bobbin with the post squeezed slightly to provide a desired amount of friction between the central posts and the cylindrical hub walls. The friction keeps the bobbin from unwinding, however the friction is not so great that it keeps the thread or floss from pulling smoothly and evenly from the bobbin. In this way the spool is secured to prevent it from rotating or unwinding when the thread is not being removed from the spool.

The MULTIPLE LOCK DENTAL FLOSS HOLDER of the present invention comprises a body having a handle portion, an intermediate portion for housing a spool of dental floss, and a forked end portion including two spaced arms, each arm having at least one floss receiving slot at a distal end thereof whereby a taut length of dental floss can be held in the slots across a span between the arms. The intermediate portion has a through bore opening on one side into a spool receiving cavity and on the other side onto an irregular surface. The body is cooperative with a spool enclosure piece or a spool enclosing base which is received into the spool receiving cavity. The spool enclosure piece has an annular cavity about a central hub for receiving a spool of dental floss. In this embodiment, the hub extends through the through bore of the intermediate portion for connection with an end cap adjacent the irregular surface of the intermediate portion. In some spool enclosing base embodiments a positional pin or a connection pin extends through the through bore of the intermediate portion for connection with a latching cap or an end cap, respectively, adjacent the irregular surface of the intermediate portion. In yet another spool enclosing base embodiment, a pin having a base portion, a neck portion and a distal end extends through the through bore of the intermediate portion. The distal end of the pin includes a groove and a taper on its outer surface. The pin cooperates with a seating hub of the spool enclosing base. In all arrangements, the MULTIPLE LOCK DENTAL FLOSS HOLDER of the present invention detentes the floss to keep it taut by four positive locking mechanisms, namely: (1) gripping means including the irregular surface (preferably a series of concentric annular grooves) of the intermediate portion for selectively locking in place a length of dental floss between an end cap or latching cap or a pin having a base portion and a neck portion and the irregular surface of the intermediate portion wherein the end cap or latching cap or pin has a cooperative irregular surface for coupling in a mating engagement with the adjacent irregular surface of the intermediate portion and is capable of axial movement upon a hub or a positional pin or a connection pin to a position of non-mated engagement or to a position of mated engagement of the cooperative irregular surfaces to thereby, respectively, selectively allow release or capture of a length of dental floss between the cooperative irregular surfaces of the end or latching cap and adjacent intermediate portion; (2) coupling means between the end cap or latching cap or pin base portion and the hub or positional pin or connection pin permitting selective pressure against a length of dental floss positioned between the end cap or latching cap or pin base portion and the irregular surface of the intermediate portion wherein a spool enclosure piece or a spool enclosing base and the end cap or latching cap or pin base portion are oppositely aligned from each other at separate ends of the hub or positional pin or connection pin, such that either the distal end of the hub or positional pin or connection pin is received in a central cavity or bore of the end cap or latching cap or the distal end of the pin having a base portion and a neck portion is received in a seating hub of the spool enclosing base so that the spool enclosure piece or spool enclosing base and end cap or latching cap or pin base portion and pin neck portion can cooperate with each other to thereby place additional pressure upon a length of dental floss to prevent slippage; (3) means for unidirectional dispensing and collection of thread to prevent release of tension in the dispensed dental floss comprising the spool enclosure piece or spool enclosing base having an annular skirt rearwardly extending from a flange cap, the external surface of which includes either a plurality of guide teeth cooperative with a ratcheting mechanism or a plurality of ratcheting mechanisms in the side wall of the spool receiving cavity of the intermediate body portion or a ratcheting mechanism or a plurality of ratcheting mechanisms cooperative with a plurality of guide teeth in the side wall of the spool receiving cavity of the intermediate body portion, to allow rotation of the spool enclosing piece in one direction only while preventing rotation in an opposite direction that would release the tension on the floss; and (4) after the floss has been threaded through the slots of the forked end portion, it is passed through a slit or groove path on the upper surface of the flange cap of the spool enclosure piece or spool enclosing base and knotted to securely fasten the floss to the flange cap so that when the flange cap is rotated in its one direction new floss is dispensed from the spool and used floss is collected under the flange of the flange cap.

In a preferred embodiment of the present invention the flange cap of the spool enclosure piece or spool enclosing base contains a pattern of groove paths which form floss indexing means to assist the user of the subject MULTIPLE LOCK DENTAL FLOSS HOLDER to replace in a measured manner the operative length of dental floss held taught between the holder's spaced arms with a corresponding length of new dental floss.

The SPOOL ENCLOSURE ASSEMBLY for use in a dental floss holder having a through bore opening on one side into a spool receiving cavity and on the other side onto an irregular surface comprises a spool enclosure piece or spool enclosing base dimensioned to be received in the spool receiving cavity which has an annular cavity about a central hub, a plurality of legs, or a central seating hub for receiving a spool of dental floss. The central hub of the spool enclosure piece or a positional pin or connection pin having one end thereof retained in the spool enclosing base extends through the through bore of the dental floss holder to cooperate with an end cap or latching end cap having an irregular surface for coupling in a mating engagement with the irregular surface of the dental floss holder such as to establish a position of non-mated engagement or a position of mated engagement of the irregular surfaces to thereby, respectively, selectively allow release or capture of a length of dental floss between the irregular surface of the end cap or latching end cap and the irregular surface of the dental floss holder. Alternatively, the distal end of a pin having a base portion and a neck portion extends through the through bore of the dental floss holder such that an annular notch in the pin's distal end cooperates with a plurality of legs or a seating hub of an alternative spool enclosing base to achieve the coupling in a mated engagement of the irregular surface formed by the pin's base portion and neck portion or an alternative pin's base portion, platform portion and neck portion with an adjacent complimentary irregular surface of the holder's intermediate portion through-bore.

The present invention has numerous advantages over prior art dental floss holders and dispensers. For example, some floss holders fail to have positive locking mechanisms and therefore floss is allowed to give when forcing it between tightly opposing teeth thereby rendering the same non-functional. The multiple positive locking mechanisms of the present invention are designed to maintain a length of dental floss in a taut condition. Further, some floss holders have complicated threading instructions which make the product difficult to use and therefore, tend to lead to discontinued use. Other floss holders require the floss to be threaded, knotted, or wrapped with respect to each usable length of floss. In this regard, each time floss is dispensed, one must unwrap the old floss, cut it off and re-thread the floss holder. By comparison, the present invention is easier to use because it needs only to be threaded one time and the thread is not removed until the entire spool has been dispensed. Further, some floss holders have a problem with the floss coming off the holder during use. The present invention preferably provides for a U-shape forked end portion including two spaced arms made to be more rigid, thus preventing flexing of the two spaced arms under pressure and a loss of floss tautness, allowing the floss to come off one or both of the spaced arms. Additionally, the spaced arms have generally deeper floss receiving guide slots and the floss is threaded in such a fashion as to wrap around the two spaced arms, inside to outside and outside to inside respectively, which forces the floss to follow the contour of the spaced arms thus preventing sagging of the floss and its dislodgement from the spaced arms. Still further, unlike some floss holders which are designed to be completely disposable, the body of the subject MULTIPLE LOCK DENTAL FLOSS HOLDER is reusable., while the SPOOL ENCLOSURE ASSEMBLY therefor may serve as a separate reusable or disposable packaging to house a replacement spool of floss. Further, although some floss holders require 12 to 18 inches of floss per use, the present invention by comparison requires as little as one inch of floss per use. One must simply advance the floss only the distance necessary to replace the length of dental floss held taut between spaced arms to replace old floss with new floss; floss indexing means of the subject MULTIPLE LOCK DENTAL FLOSS HOLDER assists the user in such advancement. Still further, some floss holders do not fit well in the hand and are difficult to properly orient for flossing. The present MULTIPLE LOCK DENTAL FLOSS HOLDER is of reduced bulk, and streamlined with the forked end portion preferably extending from the body at an oblique angle to the handle for easy insertion and manipulation in the mouth. Also, the handle of the body is of streamlined shape and preferably has a hole such that it can be stored in a toothbrush holder or hung from a hook. Still further, although some floss holders are complicated requiring several parts that are either difficult to mold and/or assemble, the present invention consists of a contiguous body and a spool enclosure assembly which may be inexpensively mass produced and easily assembled.

SUMMARY OF THE INVENTION

According to the present invention there is provided a dental floss holder for receiving a spool of dental floss and dispensing and maintaining a length of the dental floss in a taut condition comprising:
  a body having a handle portion, an intermediate portion for housing a spool of dental floss, and a forked end portion including two spaced arms, each arm having at least one floss receiving slot at a distal end thereof whereby a taut length of dental floss can be held in the slots across a span between the arms, the intermediate portion having a through bore opening on one side into a spool receiving cavity and on the other side onto an irregular surface;
  a spool enclosure piece received in the cavity and having an annular cavity about a central hub for receiving a spool of dental floss, the hub extending through the through bore, and an end cap connected to the hub adjacent the irregular surface;
  coupling means between the end cap and the hub permitting selective pressure against a length of floss positioned between the cap and the irregular surface;
  gripping means including the irregular surface for selectively locking in place the length of dental floss positioned between the cap and the irregular surface; and
  means for unidirectional dispensing and collecting the dental floss across the arms to prevent release of tension in the dispensed length of dental floss.

In another embodiment, the dental floss holder includes a spool enclosing base, received in the spool receiving cavity, which has an annular cavity about a plurality of legs for receiving a spool of dental floss, wherein the legs are capable of encapturing and retaining the distal end of a positional pin inserted therebetween. The positional pin has a stem extending through a central bore of a latching end cap and the through bore of the intermediate portion. This embodiment likewise has coupling means, gripping means, and means for unidirectional dispensing and collecting of the dental floss.

In another embodiment the dental floss holder includes a spool enclosing base, received in the spool receiving cavity, which has an annular cavity about a central seating hub for receiving a spool of dental floss, wherein the central seating hub is capable of encapturing and retaining the distal end of a connection pin inserted therein. The connection pin has a stem extending through a central bore of an end cap and the through bore of the intermediate portion. This embodiment likewise has coupling means, gripping means, and means for unidirectional dispensing and collecting of the dental floss.

In a preferred embodiment, the dental floss holder includes a pin having either a base portion, neck portion, stem portion, and distal end or a base portion, platform portion, neck portion, stem portion, and distal end which is cooperative with the spool enclosing base, received in the spool receiving cavity, which has an annular cavity about a seating hub for receiving a spool of dental floss wherein the hub is capable of either encapturing and retaining the distal end of the pin or allowing passage of the distal end through the hub, when the distal end is inserted through the through bore of the intermediate portion of the body of the dental floss holder and into the hub. This embodiment also has coupling means, gripping means, and means for unidirectional dispensing and collecting of the dental floss.

The flange cap of the spool enclosure piece or spool enclosing base of the various embodiments of the present invention preferably contains a pattern of groove paths which form floss indexing means to assist the user of the subject MULTIPLE LOCK DENTAL FLOSS HOLDER to replace in a measured manner the operative length of dental floss held taught between the holder's spaced arms with a corresponding length of new dental floss.

According to the present invention there is also provided a SPOOL ENCLOSURE ASSEMBLY for use in a dental floss holder having a through bore opening on one side into a spool receiving cavity and on the other side onto an irregular surface which comprises a spool enclosure piece or spool enclosing base dimensioned to be received in the spool receiving cavity that has an annular cavity about a central hub, a plurality of legs, or a central seating hub for receiving a spool of dental floss. The central hub of the spool enclosure piece, the pin cooperative with the seating hub of the spool enclosing base, or a positional pin or connection pin having one end thereof retained in the spool enclosing base, extends through the through bore of the dental floss holder such that an end cap or latching end cap or pin base portion and pin neck portion having an irregular surface for coupling in a mating engagement with the irregular surface of the dental floss holder establishes a position of non-mated engagement or a position of mated engagement of the irregular surfaces to thereby, respectively, selectively allow release or capture of a length of dental floss between the irregular surface of the end cap or latching end cap or pin base and the irregular surface of the dental floss holder.

Additional features and advantages of the present invention will become apparent to those skilled in the art from the following description and the accompanying figures illustrating the preferred embodiment of the invention, the same being the present best mode for carrying out the invention.

BRIEF DESCRIPTION OF THE DRAWINGS

FIG. 6 is a side view of another embodiment of the multiple lock dental floss holder constructed according to the teachings of the present invention.

FIG. 7 is a side view of the embodiment of the multiple lock dental floss holder illustrated at FIG. 6 and shows a spool enclosure assembly and a spool of dental floss exploded from a contiguous body.

FIG. 15 is a bottom view of an alternative embodiment of a spool enclosing base of the spool enclosure assembly of a preferred embodiment of a multiple lock dental floss holder.

FIG. 16 is a cross-sectional view of the spool enclosing base shown at FIG. 15, and is taken along line 16—16 of FIG. 15.

FIGS. 17A and 17B are perspective views respectively of two pins, each of which cooperates with the spool enclosing base illustrated at FIGS. 15 and 16 above.

FIGS. 19A and 19B are cross-sectional views of an alternative preferred embodiment of the multiple lock dental floss holder and shows the alternative spool enclosing base illustrated at FIGS. 15 and 16 cooperative with the distal end of the pin of FIG. 17B to establish a lock position as shown at FIG. 19A or an unlock position as shown at FIG. 19B.

FIG. 20 is a bottom perspective view of the preferred embodiment of the multiple lock dental floss holder shown at either FIG. 18A or 19A.

FIG. 21 is top perspective view of the preferred embodiment of the multiple lock dental floss holder shown at either FIG. 18A or 19A and shows a pattern of groove paths on the flange cap of the alternative spool enclosing base which pattern forms floss indexing means.

DESCRIPTION OF THE PREFERRED EMBODIMENTS

Figure 1:
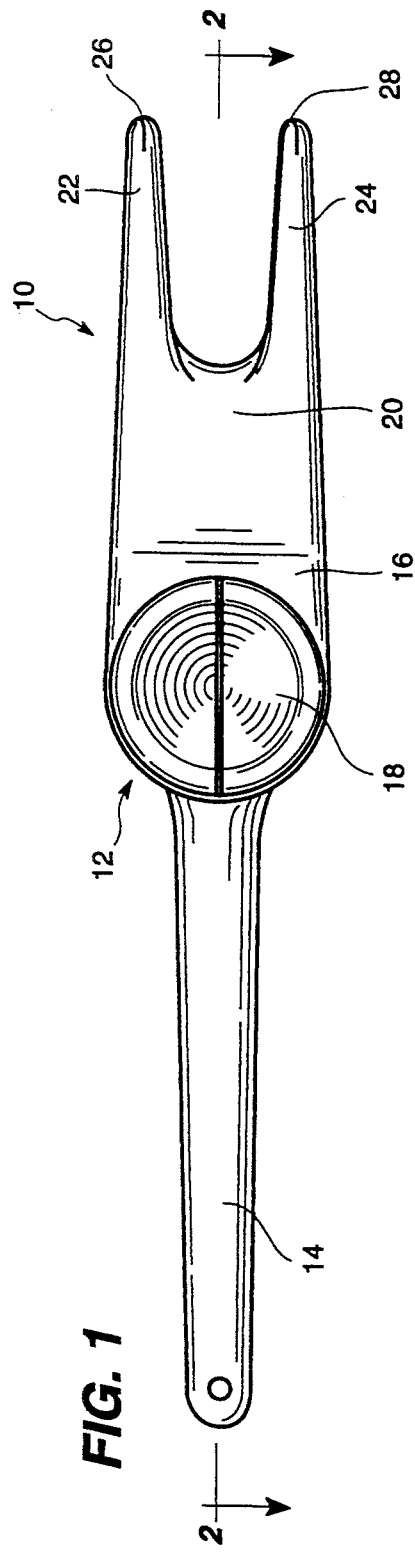
FIG. 1 is a top view of a multiple lock dental floss holder constructed according to the teachings of the present invention.

Referring now to FIG. 1, there is shown therein a top view of a multiple lock dental floss holder 10 of the present invention. Dental floss holder 10 comprises a contiguous body 12 having a handle portion 14 an intermediate portion 16 including spool enclosure piece 18, and a forked end portion 20 having two spaced arms 22 and 24, each arm having at least one floss receiving slot 26 and 28 respectively at a distal end thereof whereby a taught length of dental floss can be held in the slots 26 and 28 across the span between arms 22 and 24.

Figure 2:
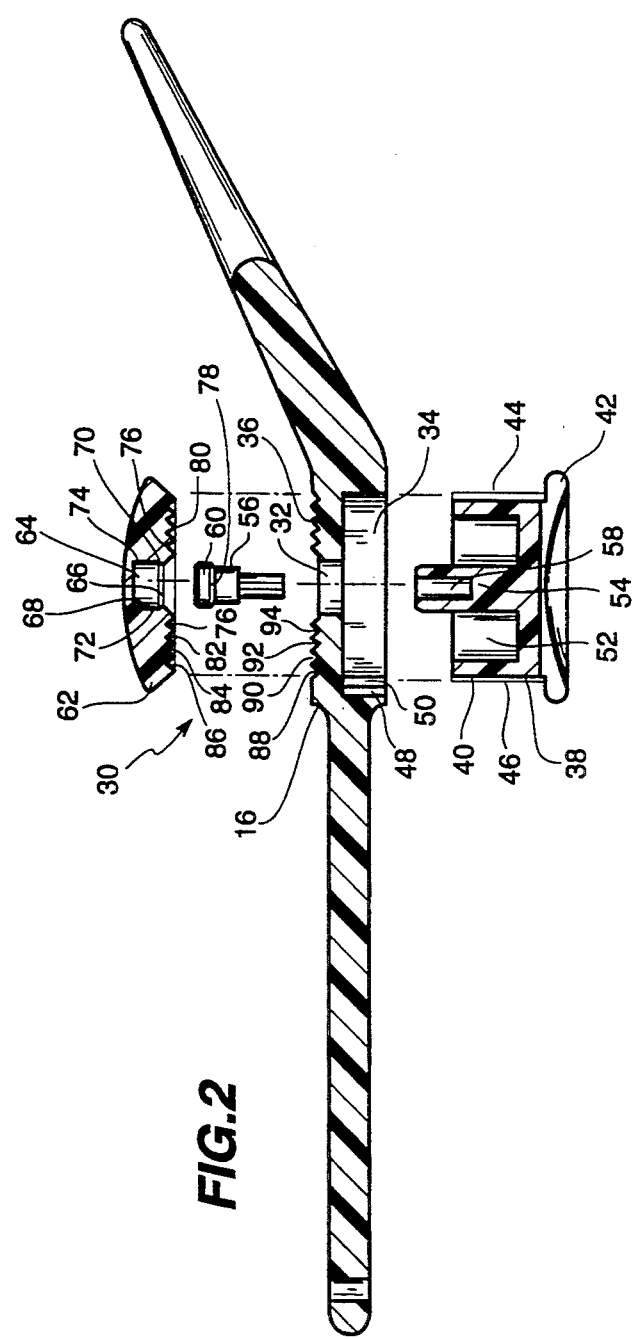
FIG. 2 is a longitudinal cross-sectional view, is taken along line 2—2 of FIG. 1 and shows a spool enclosure assembly exploded from a contiguous body.

FIG. 2 is a longitudinal cross-sectional view, is taken along line 2—2 of FIG. 1 and shows a spool enclosure assembly 30 exploded from contiguous body 12. The spool enclosure assembly 30, and contiguous body 12 may be fabricated of various thermoplastic materials such as polypropylene, polyethylene, polyethylene terephthalate, nylon, or ABS Plastic by conventional injection molding techniques known to those skilled in the art. The intermediate portion 16 of contiguous body 12 has a through bore 32 opening on one side into a spool receiving cavity 34 and on the other side to an irregular surface 36. The spool enclosure assembly 30 cooperates with intermediate portion 16 to enclose a spool of dental floss therein. The spool enclosure assembly 30 comprises a spool enclosure piece 38 dimensioned to be received in the spool receiving cavity 34 of the intermediate portion 16. The spool enclosure piece 38 has an annular skirt 40 rearwardly extending from a flange cap 42. Annular skirt 40 has at its external surface a plurality of guide teeth, such as guide teeth 44 and 46 shown in FIG. 2, which are cooperative with a ratcheting mechanism 48 in the side wall 50 of the spool receiving cavity 34 of the intermediate portion 16 to allow rotation of the spool enclosure piece 38 in one direction only while preventing rotation in its opposite direction. The spool enclosure piece 38 has an annular cavity 52 about a central hub 54 within the annular skirt 40 for receiving a spool of dental floss.

Central hub 54 is an integral piece, however, for purposes of illustration, it is shown exploded at FIG. 2 with connector piece 56 separated from central hollow bore 58 of central hub 54. Connector piece 56 may be solvently bonded into central hollow bore 58 of central hub 54, and in this regard the external wall of central hub 54 may be provided with a slit extending into the central hollow bore of the hub such that air is dissipated therethrough during insertion of said connector piece 56 into the central hollow bore 58 of the hub. The integral central hub 54 with connector piece 56 extends through the through bore 32 of the intermediate portion 16 which opens on one side into the spool receiving cavity 34 and on the other side to an irregular surface 36.

FIG. 2 shows that the central hub 54, particularly the distal end 60 of connector piece 56, cooperates with end cap 62 to constitute coupling means between the end cap 62 and central hub 54 permitting selective pressure against a length of dental floss positioned between the end cap 62 and irregular surface 36 of intermediate portion 16. In this regard, central hub 54 extends through the through bore 32 of the intermediate portion 16 such that the distal end 60 of the central hub 54 can be received in central cavity 64 of end cap 62. Central cavity 64 has two diameters, namely a first narrower diameter 66 at upper frictional point portions 70 and 72 of the cavity and a second greater diameter 68 at the lower portion 74 of central cavity 64. The first and second diameters 66 and 68 permit selective pressure against a length of dental floss positioned between the end cap 62 and the irregular surface 36 since, as the spool enclosure piece 38 and end cap 62 are oppositely aligned from the other at separate ends of central hub 54, when the distal end 60 of the central hub is received in central cavity 64 of end cap 62, the spool enclosure piece and end cap are capable of depression towards each other by the fingers of a user to apply selective pressure against the length of dental floss. Specifically, distal end 64 of central hub 54 upon encountering the first narrower diameter of end cap central cavity 64 at upper frictional point portions 70 and 72 will laterally outwardly display the upper frictional point portions 70 and 72 allowing the distal end 60 to pass axially below the same until the distal end is received in the second greater diameter lower portion 74 of central cavity 64 of end cap 62. The annular groove 76 of end cap 62 may be removed and replaced with a trough (such as trough 150, shown at FIGS. 5A and 5B) in order to promote additional laterally outward flexing of the upper frictional point portions 70 and 72 of the end cap 62 when the distal end of the hub is received into the central cavity of the end cap. The greater diameter lower portion 74 of central cavity 64 of the end cap 62 is of a length greater than the length of the distal end 60 such that when the distal end is fully seated within the greater diameter lower portion 74 of the central cavity 64 there is preferably approximately an eighth of an inch of space between the proximal edge 78 of distal end 60 and upper frictional point portions 70 and 72. Since spool enclosure piece 38 and end cap 62 are oppositely aligned from the other at separate ends of the central hub 54, the additional spacing within the second greater diameter of central cavity 64 of the end cap 62 allows the end cap 62 and spool enclosure piece 38 to be depressed towards each other by the fingers of a user to apply selective pressure against a length of dental floss positioned between the irregular surface 36 of intermediate portion 16 and end cap 62.

FIG. 2 also shows that an irregular surface 36 of intermediate portion 16 cooperates with a complimentary irregular surface 80 of an end cap 62 to achieve a mated engagement comprising gripping means that selectively allows release or capture of a length of dental floss positioned between irregular surface 36 of intermediate portion 16 and end cap 62. In this regard, end cap 62 is capable of limited axial movement upon central hub 54 due to the additional depth of spacing with respect to the distal end 60 within the greater diameter lower portion 74 to a position of non-mated engagement or to a position of mated engagement of the irregular surfaces 36 and 80 to thus thereby, respectively, selectively allow release or capture of a length of dental floss between the irregular surface 36 of intermediate portion 16 and the adjacent irregular surface 80 of end cap 62.

The particular configuration of irregular surface 36 of intermediate portion 16 and adjacent complimentary irregular surface 80 of end cap 62 may be of various embodiments, so long as they cooperate with each other to achieve a mating engagement. For example, as shown in FIG. 2, the adjacent complimentary irregular surface 80 of end cap 62 may comprise a first plurality of concentric angular grooves 86, 84, 82, and 76 on its inwardly facing external surface for coupling in a mating engagement with a correspondingly cooperative second plurality of concentric angular grooves 88, 90, 92, and 94 on the external surface of the irregular surface 36 of intermediate portion 16. In this structure, end cap 62 is capable of limited axial movement upon the central hub 54 to a position of non-mated engagement or to a position of mated engagement to thereby, respectively, selectively allow release or capture of a thread of dental floss between the first and second plurality of cooperative concentric angular grooves. As will be apparent to those skilled in the art, the first and second plurality of cooperative concentric angular grooves shown at FIG. 2 may be replaced with a male/female mating structure of various configurations wherein a male or female portion of an irregular surface of end cap 62 is capable of being received, respectively, into a female or male portion of irregular surface 36 of intermediate portion 16 to achieve a mating engagement. The teaching of the present invention and claims thereof contemplate any irregular surfaces cooperating to achieve a mating engagement.

Figure 3:
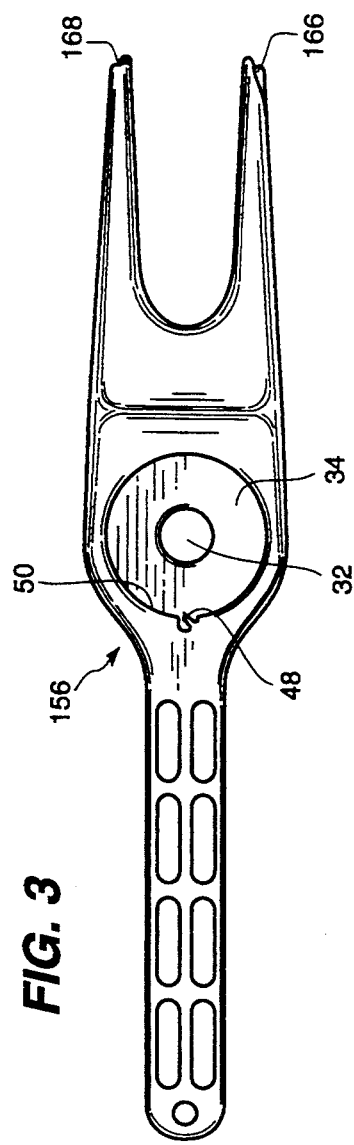
FIG. 3 is a top view of the contiguous body of a multiple lock dental floss holder similar to FIG. 1, but showing a different handle and different floss receiving slots at the distal end of the two spaced arms.
Figure 4:
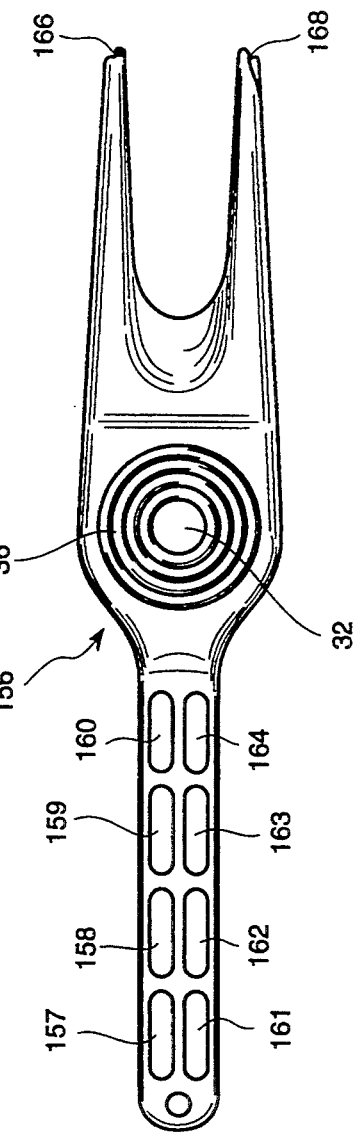
FIG. 4 is a bottom view of the contiguous body of the multiple lock dental floss holder shown at FIG. 3.
Figure 5A:
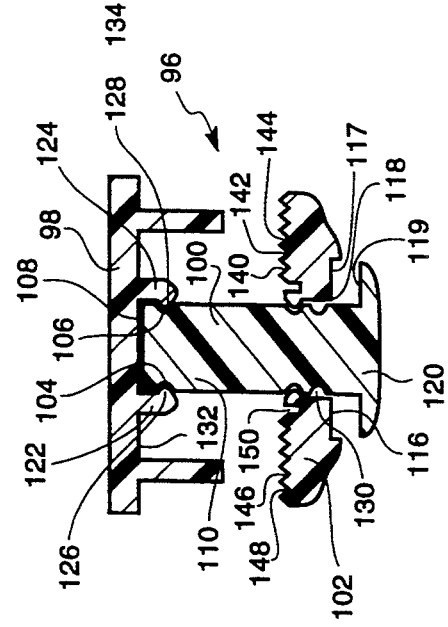
FIG. 5 is a cross-sectional view of an alternative spool enclosure assembly comprising a spool enclosing base capable of engagement with the distal end of a positional pin designed to accommodate axial movement of a latching end cap thereon to establish a locked position as shown at FIG. 5A or an unlocked position as shown at FIG. 5B for a multiple lock dental floss holder.
Figure 5B:
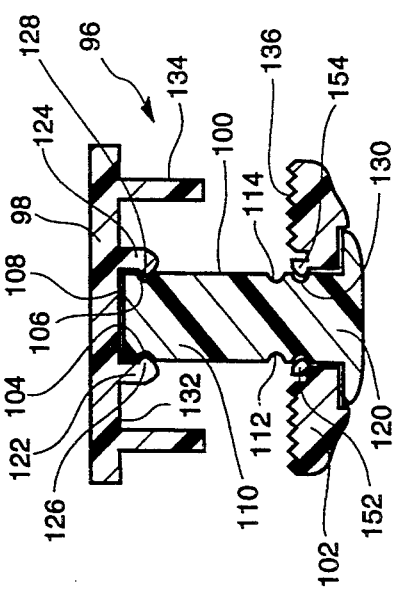

Referring now to FIGS. 5A and 5B, there is shown in cross-sectional view an alternative spool enclosure assembly 96 for use with respect to a contiguous body of the multiple lock dental floss holder as illustrated at FIGS. 1, 3, 4, 6 and 7. Spool enclosure assembly 96 consists of a spool enclosure base 98, a positional pin 100 and a latching end cap 102. The positional pin 100 has a pair of notches 104 and 106 disposed near distal end 108, a stem 110, a first set of notches 112 and 114 defining a locked position of the positional pin disposed in said stem 110, and a second set of notches 116 and 118 defining a unlocked position near proximal head 120 of the positional pin. Distal end 108 of positional pin 100 can be set between spool enclosing base legs 122 and 124 which have inwardly facing notch retaining members 126 and 128 to frictionally hold distal end 108 between legs 122 and 124 to integrate spool enclosure base 98 with positional pin 100. When the positional pin is placed through central through bore 130 of latching end cap 102, the stem of the positional pin is of sufficient length to extend through the through bore 32 of the intermediate portion 16 of the contiguous body of the multiple lock dental floss holder in its various embodiments to be engaged with the spool enclosing base 98 when the spool enclosure base is received in the spool receiving cavity 34 of intermediate portion 16 to enclose a spool of dental floss in the annular cavity 132 which is bordered on the outside by spool enclosing base annular skirt 134 and inwardly by legs 122 and 124. Latching end cap 102 has an inwardly facing irregular surface 136 cooperative with a complimentary irregular surface of the intermediate portion of the multiple lock dental floss holder in its various embodiments to achieve a mating position therewith. For example, irregular surface 136 of latching end cap 102 shown in FIGS. 5A and 5B may consist of a plurality of concentric angular grooves 140, 142, 144, 146 and 148 which terminates laterally inwardly into annular trough 150 adjacent to brace projections 152 and 154. Brace projections 152 and 154 cooperate with lock position notches 112 and 114 or unlock position notches 116 and 118 of stem 110 of the positional pin 100 to selectively engage the positional pin in either an locked position shown at FIG. 5A wherein dental floss is secured between the joined irregular surfaces of the intermediate portion of the contiguous body and latching end cap or an unlocked position shown at FIG. 5B where floss may be freely advanced between separated irregular surfaces. The locked position of FIG. 5A, where brace projections 152 and 154 are set into lock position notches 112 and 114 of positional pin stem 110, provides for a joining of the irregular surface of the latching end cap to the irregular surface of the intermediate portion of the contiguous body while the unlocked position of FIG. 5B, where brace projections 152 and 154 are set into unlock position notches 116 and 118 of positional pin stem 110, provides for a separation of the irregular surfaces. The distance between lock position notches 112 and 114 and unlock position notches 116 and 118 corresponds to the distance of travel of the seating surface 119 of proximal head 120 to and from the stop ledge 117 of end cap 120. When the spool enclosure assembly 96 is in the unlocked position shown at FIG. 5B, a user may push in on the outside portion of end cap 120 to disengage brace projections 152 and 154 from unlock position notches 116 and 118 of stem 110 into lock position notches 112 and 114 to achieve the locked position shown at FIG. 5A. When the spool enclosure assembly 96 is in the locked position, a user may push in on positional pin 100 to disengage brace projections 152 and 154 from lock position notches 112 and 114 of stem 110 into unlock position notches 116 and 118 to achieve the locked position shown at FIG. 5B.

The coupling means between latching end cap 102 and positional pin 100 permitting selective pressure against a length of dental floss positioned between latching end cap 102 and the irregular surface of the contiguous body intermediate portion comprises spool enclosing base 98 and latching end cap 102 being oppositely aligned from the other at separate ends of positional pin 100 with the stem 110 of the positional pin being received in central through bore 130 of the latching end cap such that the spool enclosing base 98 and latching end cap 102 are capable of depression towards each other by the fingers of a user to apply selective pressure against said length of dental floss.

FIGS. 3 and 4 illustrate another embodiment of the contiguous body of the MULTIPLE LOCK DENTAL FLOSS HOLDER constructed to the teachings of the present invention.

As observed at FIGS. 3 and 4, the contiguous body 156 of the preferred embodiment of the MULTIPLE LOCK DENTAL FLOSS HOLDER is similar to the previous embodiments excepting that the handle thereof is provided with a plurality of elongated holes 157 through 164 to dissipate heat and reduce cost of molding, and the forked ends portions of the two spaced arms have different floss receiving slots 166 and 168 conducive to the proper directional positioning and orientation of the length of dental floss disposed therein.

FIG. 6 illustrates in side view another embodiment of a contiguous body and spool enclosure assembly of the present invention. FIG. 7 illustrates in an inverted side view the MULTIPLE LOCK DENTAL FLOSS HOLDER and SPOOL ENCLOSURE ASSEMBLY of FIG. 6 and shows the spool enclosure assembly and a spool of dental floss exploded from a contiguous body.

The spool enclosure assembly 170 shown exploded from the contiguous body 156 at FIG. 7 includes spool enclosing base 172 which has an annular skirt 174 rearwardly extending from flange cap 176. The external surface annular skirt 174 includes a plurality of guide teeth 175 cooperative with a single ratcheting mechanism or a plurality of ratcheting mechanisms in the side wall of the spool receiving cavity of the intermediate portion of the contiguous body of the multiple lock dental floss holder to allow rotation of the spool enclosure piece in one direction while preventing rotation in its opposite direction.

Figure 8:
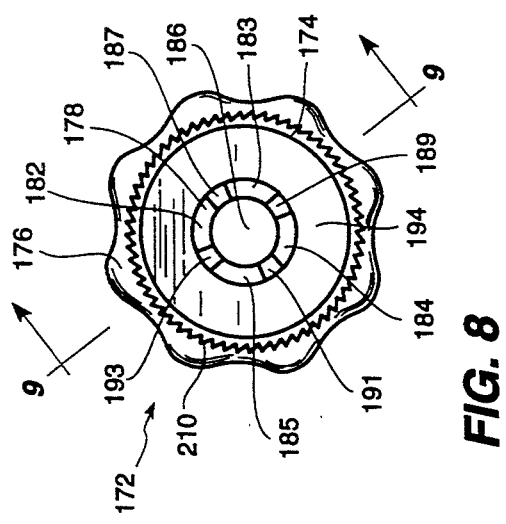
FIG. 8 is a bottom view of one embodiment of a spool enclosing base of the spool enclosure assembly of the preferred embodiment of the multiple lock dental floss holder shown at FIGS. 6 and 7.
Figure 9:
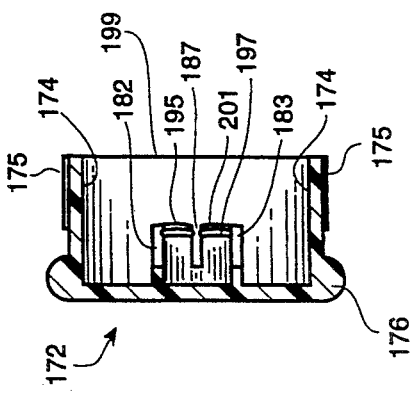
FIG. 9 is a cross-sectional view of the spool enclosing base shown at FIG. 8, and is taken along line 9—9 of FIG. 8.

At FIG. 8 there is illustrated a bottom view of one embodiment of spool enclosing base 172 of the spool enclosure assembly 170 shown at FIGS. 6 and 7. Between the annular skirt 174 and a central seating hub 178 of the spool enclosing base 172 is an annular cavity 194 which is dimensioned to receive the dental floss spool 180 shown at FIG. 7. Central seating hub 178 is capable of encapturing and retaining in a forced fit the distal end 188 of a connection pin 190 inserted therein. As best shown in the bottom view of FIG. 8, central seating hub 178 consists of a plurality of legs 182, 183, 184 and 185 rearwardly extending from flange cap 176 and equidistantly separated and spaced from each other by apertures 187, 189, 191, and 193 to thereby define a central receiving aperture 186. As best shown in FIG. 9, which is a cross-sectional view of the spool enclosing base 172 shown at FIG. 8 taken along line 9—9 thereof, each of the plurality of legs, such as legs 182 and 183, has a latching lip 195, 197 near leg end surface 199 and 201 respectively. The latching lip of each of the plurality of legs cooperates with the taper 203 of distal end 188 of connection pin 190 (see FIG. 12) to encapture and retain in a forced fit distal end 188 when connection pin 190 is inserted in central seating hub 178. Specifically, central receiving aperture 186 is disposed in axial alignment with seating end surface 192 of the distal end 188 of connection pin 190. When distal end 188 is inserted into central seating hub 178, end surface 192 contacts the latching lip of each of the plurality of legs (such as latching lips 195 and 197 shown at FIG. 9) and outwardly laterally displays the same until distal end 188 is fully seated in central receiving aperture 186 whereupon, due to the taper 203 of distal end 188, the latching lips return to their pre-displacement position to encapture and retain distal end 188. In this regard, the latching lips define a first narrower diameter to the central seating hub which is temporarily displayed to allow entry of the distal end 188 into a second greater diameter of the central seating hub. Apertures 187, 189, 191, and 193 promote the outward lateral display of the plurality of legs.

Figure 13:
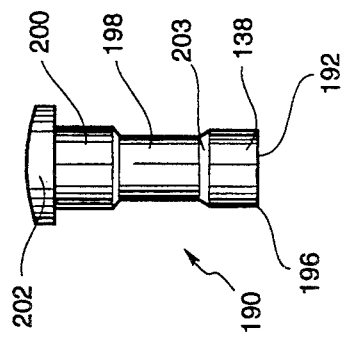
FIG. 13 is a top view of a through bore end cap of the spool enclosure assembly of the multiple lock dental floss holder embodiment shown at FIGS. 6 and 7 and shows a plurality of concentric annular grooves surrounding a through bore.
Figure 12:
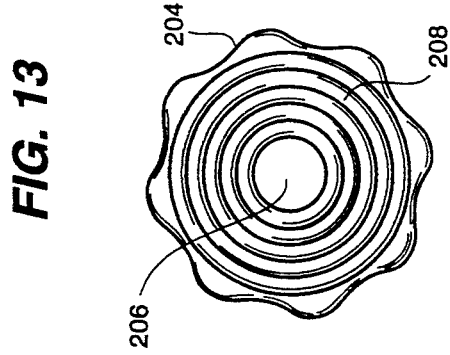
FIG. 12 is a perspective view of the connection pin of the multiple lock dental floss holder embodiment shown at FIGS. 6 and 7.

As shown at FIG. 12, the connection pin 190 has stem 196 which consists of distal end 188, intermediate portion 198 and bottom portion 200 which terminates into pin head 202. Connection pin 190 cooperates with spool enclosing base 172 and end cap 204. The stem 196 of the connection pin 190 extends through a central bore 206 of end cap 204 (see FIG. 13) and also the through bore of the intermediate portion of the contiguous body in its various embodiments such that distal end 188 of the connection pin 190 can be encaptured and retained in central seating hub 178 of the spool enclosing base 172.

The embodiment of the multiple lock dental floss holder illustrated at FIGS. 6 and 7 establishes coupling means, gripping means, and means for unidirectional dispensing and collecting of dental floss similar to the previous embodiments of the present invention. In particular, the gripping means may include end cap 204 (shown at FIG. 13) having a central bore 206 and an irregular surface 208 for coupling in mated engagement with an adjacent complimentary irregular surface of the intermediate portion of a contiguous body of the multiple dental floss holder. Connection pin 190 is capable of axial movement with respect to the end cap 204 to establish a position of non-mated engagement or a position of mated engagement of the end cap irregular surface to an adjacent irregular surface of the intermediate portion of a contiguous body of the multiple dental floss holder to thereby, respectively, selectively allow release or capture of a length of dental floss therebetween. As pin head 202 of the connection pin 190 extends preferably approximately one-eighth inch above the externally facing outer surface of end cap 204 when distal end 188 of connection pin 190 is retained in central seating hub 178 of spool enclosing base 172, pressure applied on pin head 202 by a user's thumb causes connection pin 190 to travel to a point where pin head 202 is flush with the externally facing outer surface 208 of the end cap 204 (see FIG. 6). In so traveling, it moves the opposing spool enclosure piece by a distance equivalent to the travel of the pin and disengages the opposing complimentary irregular surfaces of the end cap and the intermediate portion of the contiguous body. By pressing down on the end cap 204, the travel of connection pin 190 is reversed and the irregular surfaces are engaged effectively locking a length of floss between the complimentary irregular surfaces. The operation of connection pin 190 and end cap 204 to establish a position of non-mated engagement or a position of mated engagement of the end cap irregular surface to an adjacent irregular surface of the intermediate portion of a contiguous body is thus similar to the spool enclosure assembly 96 discussed above in reference to FIG. 5A and 5B; however, rather than utilizing braces projections of latching end cap 102 to cooperative with the open or closed position notches of positional pin 100, the lock and unlock position of connection pin 190 and end cap 204 is established by the distance of travel of pin head 202 to and from the externally facing outer surface 208 of the end cap 204.

Similar to other embodiments previously discussed, coupling means between end cap 204 and connection pin 190 permitting selective pressure against a length of dental floss positioned between end cap 204 and the irregular surface of the contiguous body intermediate portion comprises spool enclosing base 172 and end cap 204 being oppositely aligned from the other at separate ends of connection pin 190 with the stem 196 of the connection pin 190 being received in the central bore 206 of end cap 204 such that the spool enclosing base 172 and end cap 204 are capable of depression towards each other by the fingers of a user to apply selective pressure against the length of dental floss.

Figure 10:
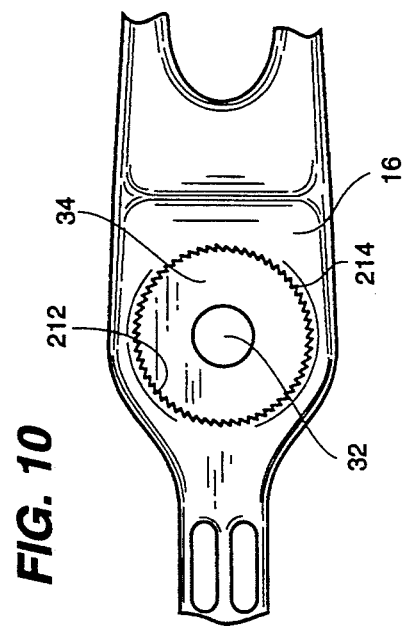
FIG. 10 is a top view of the intermediate portion of the contiguous body of an alternative embodiment of the multiple lock dental floss holder shown at FIG. 3 and shows a plurality of gear teeth at the inside wall surface of a spool receiving aperture of the intermediate portion.
Figure 11:
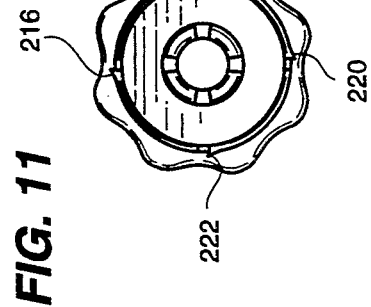
FIG. 11 is an alternative embodiment of the spool enclosing piece or base wherein an annular flange skirt of the spool enclosing piece or base is provided with a plurality of ratcheting mechanisms for interaction with the plurality of gear teeth at the inside wall surface of the spool receiving aperture of the intermediate portion shown at FIG. 10.

As shown in FIG. 8, the means for unidirectional dispensing and collection of thread may include the spool enclosing base 172 having an annular skirt 174 rearwardly extending from a flange cap 176, the external surface of which includes a plurality of guide teeth 210 cooperative with a ratcheting mechanism (such as ratcheting mechanism 48 shown in FIG. 3) or a plurality of ratcheting mechanisms in the side wall of the spool receiving cavity of the intermediate portion of the contiguous body to allow rotation of the spool enclosing base in one direction only while preventing rotation in an opposite direction. Alternatively, as shown at FIG. 10, the means for unidirectional dispensing and collection of dental floss thread can comprise the side wall 212 of the spool receiving cavity 34 of the intermediate portion 16 of the contiguous body having a plurality of guide teeth 214 cooperative with a ratcheting mechanism or a plurality of ratcheting mechanisms on the outer wall surface of the annular skirt of alternative embodiment spool enclosing base 226 (as shown at FIG. 11) to likewise allow rotation of the spool enclosing base in only one direction while preventing rotation in its opposite direction.

Whether the gear teeth cooperative with one or more ratcheting mechanisms are located in the intermediate portion of the body or the spool enclosing base, it is preferable that the gear teeth be of a sufficient number such as 60 gear teeth placed at 6° increments about the 360° annular cap.

Figure 14A:
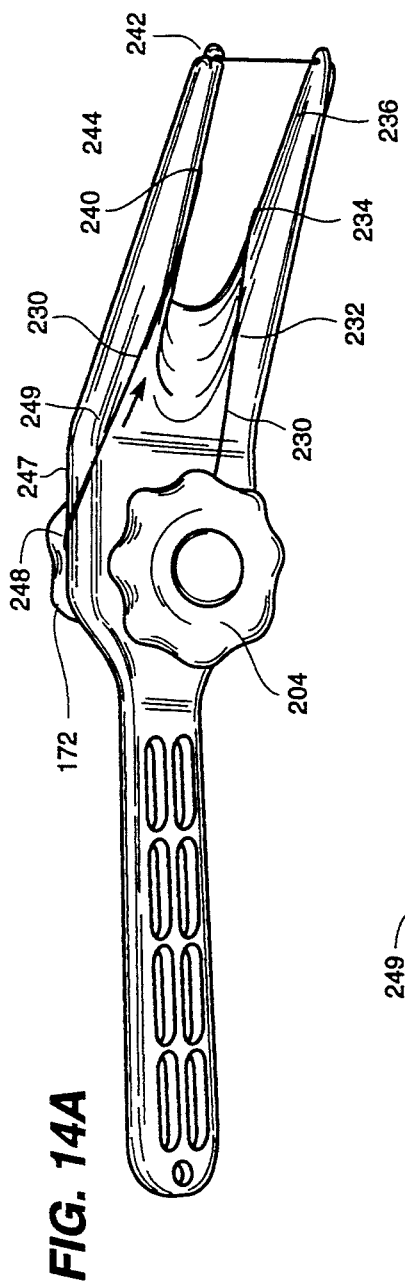
FIGS. 14A, 14B, and 14C are, respectively, side perspective, bottom, and top views of the multiple lock dental floss holder embodiment shown at FIGS. 6 and 7 showing the same bearing a taut length of dental floss held in floss guiding slots.
Figure 14B:
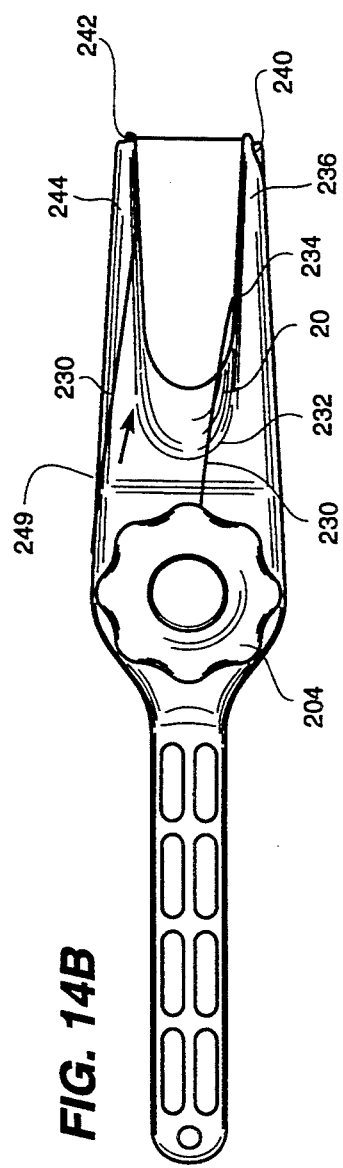
Figure 14C:
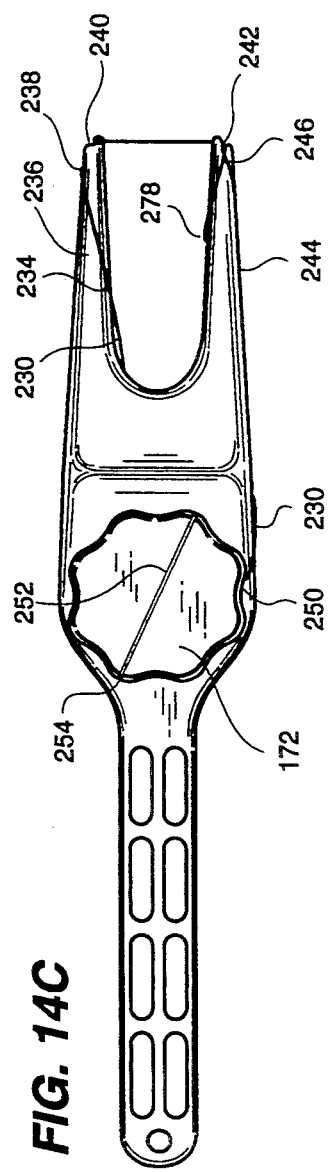

The means for unidirectional dispensing and collecting of dental floss across the spaced arms to prevent release of tension of the dispensed length of dental floss in the various embodiments of the multiple lock dental floss holder will require a user to properly dispense and orientate an initial length of dental floss. FIGS. 14A, 14B and 14C illustrate a proper setting of dental floss in the preferred embodiment of the MULTIPLE LOCK DENTAL FLOSS HOLDER. Referring now to FIGS. 14A and 14B after dental floss is dispensed from floss spool 180 initially downward past the through bore 32 of the intermediate portion 16 of the various contiguous body embodiment of the present invention, the floss thread 230 then extends along bottom surface 232 of end portion 20 of the contiguous body to an intermediary point 234 on the bottom surface of one spaced arm 236. As shown at FIG. 14C, the thread 230 then wraps around arm 236 commencing at intermediate point 234 and continuing through near distal end point 238 where, as shown at FIG. 14B, the thread of dental floss 230 is received into floss receiving slot 240 of arm 236 and is directed at a right angle to opposing floss receiving slit 242 of arm 244. The thread is then directed from opposing floss receiving slit 242 upward to an upper surface point 246 on arm 244 whereupon the thread wraps around in a reverse direction to the inside of arm 244 to lower surface point 248 of arm 244 where the thread diagonals to a thread receiving point 250 of spool enclosing base 172. In the initial threading of dental floss, the floss is threaded from receiving point 250 through and beyond the length of floss slot 252 of spool enclosing base 172 so that the floss can be knotted and reeled back to knot set point 254 of floss slot 252 by rotation of spool enclosing base 172. The continued unidirectional rotational movement of spool enclosing piece 172 will send thread along the thread path heretofore described providing a taut length of dental floss between the spaced arms while collecting old thread around neck 256 under flange cap 176.

The contiguous body of the preferred embodiment of the MULTIPLE LOCK DENTAL FLOSS HOLDER may contain a groove path for receiving a properly dispensed and orientated length of dental floss as well as indicia, such as groove path 247 and raised directional arrow 249 of FIG. 14A, for directing the user to properly dispense and orientate the length of dental floss into the groove path.

FIGS. 15 through 21 of the drawings illustrate preferred embodiments of the multiple lock dental floss holder. In FIGS. 15 and 16 there is illustrated a spool enclosing base 258 having a base through bore 260. Base through bore 260 is cooperative with pins 262 and 264, respectively, of FIGS. 17A and 17B. Pin 262 illustrated at FIG. 17A has a base portion 266, a platform portion 268 upon base portion 266, a neck portion 270 upon platform portion 268, a stem portion 272 extending from neck portion 270, and a distal end 274. Pin 264 illustrated at FIG. 17B is similar to that of the pin 262 of FIG. 17A, but has no platform portion between the pin base portion and neck portion as pin 264 includes a base portion 276, a neck portion 278, a stem portion 280 extending from the neck portion 278, and a distal end 282. The base portion 276 and neck portion 278 of pin 264, or the base portion 266, platform portion 268, and neck portion 270 of pin 262 form an irregular surface for coupling in a mated engagement with a complementary irregular surface of the intermediate portion of the body of the alternative multiple lock dental floss holder (See FIGS. 18A and 18B and 19A and 19B) similar to that in previously described embodiments of the multiple lock dental floss holder. Thus, instead of an end cap or a latching end cap through which a pin is inserted as described in previous embodiments, a pin may be provided with a base portion and neck portion, or a base portion, platform portion, and neck portion combination, as an integral design forming an irregular surface for coupling in a mated engagement with an adjacent complementary irregular surface of an intermediate portion of the multiple lock dental floss holder herein when pin 262 or pin 264 is axially moved with respect to spool enclosing base 258 to establish a position of non-mated engagement or a position of mated engagement of the irregular surfaces of the pin and intermediate portions to thereby, respectively, selectively allow release or capture of a length of dental floss between the irregular surfaces.

Figures 18A, 18B:
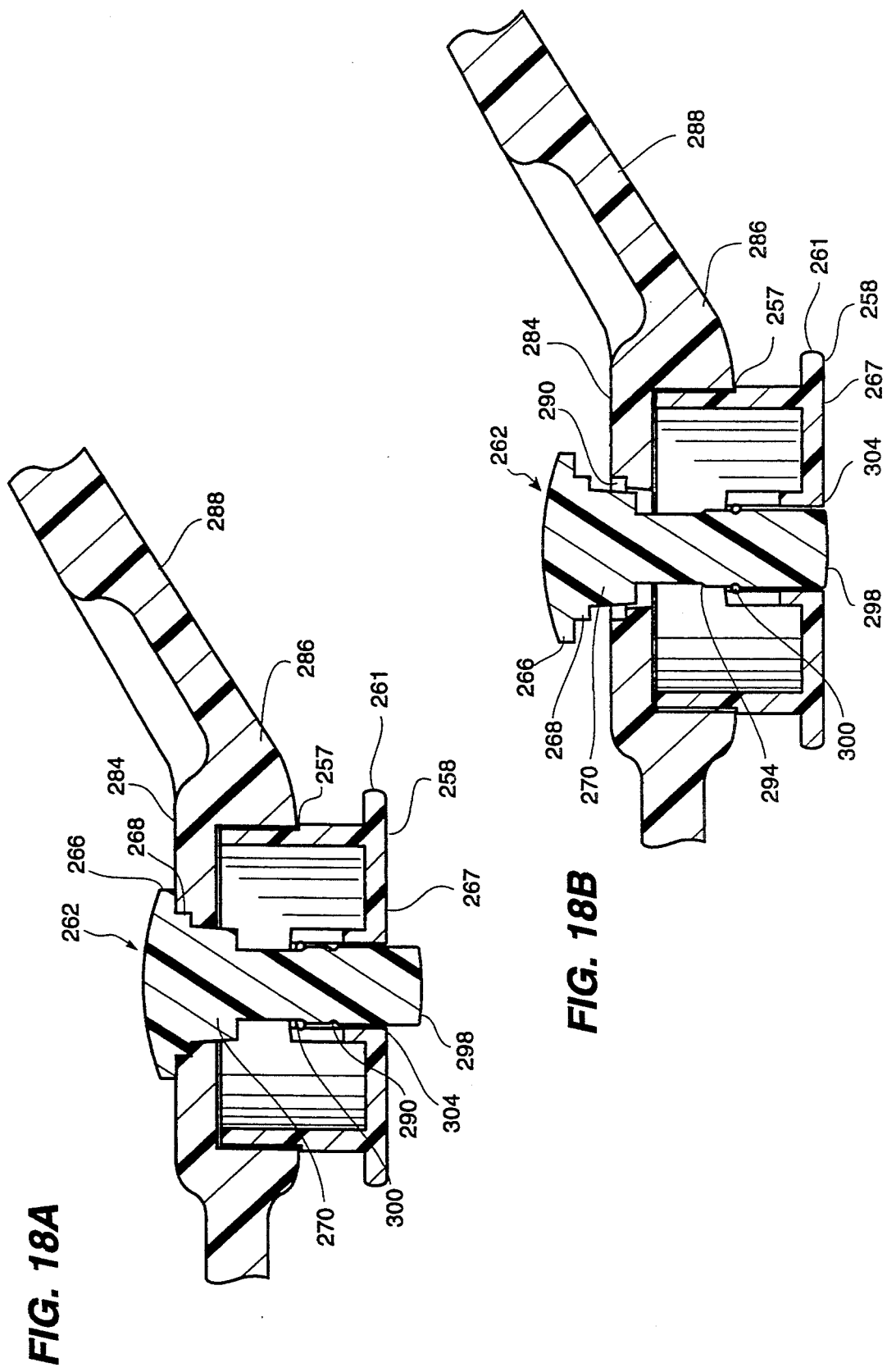
FIGS. 18A and 18B are cross-sectional views of a preferred embodiment of the multiple lock dental floss holder and shows the alternative spool enclosing base illustrated at FIGS. 15 and 16 cooperative with the distal end of the pin of FIG. 17A to establish a lock position as shown at FIG. 18A or an unlock position as shown at FIG. 18B.

FIG. 18 illustrates how pin 262 of FIG. 17A cooperates with an alternative intermediate portion 284 of contiguous body 286 of an alternative embodiment multiple lock dental floss holder 288 to achieve a non-mated or mated engagement of irregular surfaces due to axial movement of pin 262 with respect to intermediate portion 284 and spool enclosing base 258. Specifically, pin 262 may be inserted through the through bore 290 of intermediate portion 284 of the contiguous body 286 of dental floss holder 288 as in other embodiments of the invention herein such that base portion 266, platform portion 268, and neck portion 270, which neck portion has a tapered outer annular surface, to achieve a coupling mating engagement with the through bore 290 of the intermediate portion 284 to thereby, selectively allow release or capture of a thread of dental floss between the base of the pin and the intermediate portion of the dental floss holder body 288. As best shown at FIG. 17A, the distal end 274 of pin 262 is provided with annular notch 290 in its outer surface 292 and a taper 294 rearward of annular notch 290 in stem 272. Annular notch 290 and taper 294 cooperate with the plurality of legs or seating hub 296 of the alternative spool enclosing base 258 in a manner similar to that previously described as to how central seating hub 178 is capable of encapturing and retaining in a force fit distal end 188 of connection pin 190 in reference to FIGS. 8 and 9. In this regard, base through bore 290 of intermediate portion 284 is disposed in axial alignment with the seating end surface 298 of the distal end 274 of pin 262. When distal end 274 is inserted into seating hub 296, end surface 298 contacts the detent or latching lip 300 of each of the plurality of legs 296A, 296B, 296C, and 296D which collectively comprise seating hub 296 and outwardly laterally displays the same until annular notch 290 receives the detent or latching lip of each of the plurality of legs and thereby establishes a non-mated engagement position of the pin 262 to intermediate portion 284 and spool enclosing piece 258 as illustrated in FIG. 18B. Further pressure by finger of a user on pin base 266 of pin 262 will force intermediate stem portion 272 of pin 262 to contact the detent or latching lip 300 of each of the plurality of legs 296A, 296B, 296C and 296D and outwardly laterally display the same until the detent or latching lip encounters taper 294 of pin 262 thereby establishing a mechanical lock and a position of mated engagement shown at FIG. 18A of the irregular surface of pin 262 formed by base 266, platform 268, and neck 270 with the adjacent complementary irregular surface of intermediate portion through bore 290. In this locked position the distal end 298 of pin 262 protrudes outward of the top edge 304 of through bore 290. In this manner, the axial movement of pin 262 through the through bore 290 of intermediate portion 284 utilizes the base portion 266, platform portion 268, and neck portion 270 of pin 262 as an irregular surface cooperative with the adjacent irregular surface of the intermediate portion through bore 290 of alternative spool enclosing base 258. Pressure by a user's finger upon the protruding distal end 298 of pin 262 will reverse in axial movement pin 262 from the lock position shown at FIG. 18A to the unlock position shown at FIG. 18B.

Pin 264 illustrated at FIG. 17B operates in a similar manner with respect to the alternative spool enclosing base 258 to establish an unlock or locked position by virtue of pressure of the finger of a user upon pin 264 to thereby apply selective pressure against a length of dental floss. FIGS. 19A and 19B illustrate pin 264 in a lock and an unlock position respectively in the same manner as described with respect to FIGS. 18A and 18B with the exception that pin 264 utilizes only base portion 276 and neck portion 278 to form an irregular surface for coupling in mated engagement with the irregular surface of the intermediate portion 306 of contiguous body 310 of dental floss holder 312 established by through bore 308. There is no platform portion upon the base portion for which the neck portion of pin 264 is to sit. Accordingly, the through bore 308 of the irregular surface of intermediate portion 306 is designed to cooperatively accommodate base portion 276 and neck portion 278 of pin 264.

The tapered outer annular surface of the neck portion 270 of pin 262 or neck portion 278 of pin 264 also serves as a wedging surface (in addition to an irregular surface) cooperative with through bore 290 or 308, respectively to achieve an additional wedge locking action upon the dental floss.

The pin 262 or 264 when combined with spool enclosing base 258 forms a spool enclosing assembly.

As illustrated in FIG. 15, the alternative spool enclosing base 258 has an annular skirt 259 rearwardly extending from a flange cap 261. Alternative spool enclosing base 258 also has means for unidirectional dispensing and collection of dental floss thread by virtue of annular skirt 259 having on its outer annular surface one or more ratcheting mechanisms 263 for cooperation with a plurality of guide teeth such as the plurality of guide teeth 214 of the spool receiving cavity 34 of the intermediate portion 16 illustrated at FIG. 10 to thereby allow rotation of the alternative spool enclosing base 256 in only one direction while preventing rotation in its opposite direction. In this regard FIG. 15 illustrates ratcheting mechanisms 263 extending outward from the outer annular surface of annular skirt 259. When alternative spool enclosing base 258 is set into spool receiving cavity 34, rest edge 257 will seat upon the plurality of guide teeth 214 of side wall 212 while ratcheting mechanisms 263 rests between a pair of the guide teeth. Annular skirt 259 is preferably provided with a plurality of break channels 265 spaced from each other on either side of ratcheting mechanism 263 to thereby form a break in the circumference of the annular flange skirt 259 such that the ratcheting mechanism portion of annular flange skirt 259 between the break channels 265 may flex inward toward the seating hub 296 during unidirectional rotation of the alternative spool enclosing base 258 so as to minimize wear on ratcheting mechanisms 263.

FIG. 20 and FIG. 21 are a bottom perspective and top perspective view respectively of the preferred embodiment of the multiple lock dental floss holder in a locked position such as that shown in FIG. 18A or 19A. The means for unidirectional dispensing and collection of dental floss across spaced arms 314 and 316 of multiple lock dental floss holder 318 will require a user to properly dispense and orientate an initial length of dental floss similar in manner to that previously described with respect to FIGS. 14A, 14B and 14C. In this regard, floss thread 320 is dispensed from a floss spool initially downward through the through bore 290 of intermediate portion of 284 of the contiguous body 286 of dental floss holder 288 or through bore 308 of the intermediate portion 306 of contiguous body 310 of dental floss holder 312. Floss thread 320 then extends through floss guide channel 322 (best observed at FIG. 21) where it wraps around arm 314 to be directed at a right angle to opposing floss guide channel 324 such that it is directed upward around opposing arm 316 so that dental floss 320 may be directed back toward the alternative spool enclosing base 258 up floss guide ramp 326. In this regard floss guide ramp 326 stabilizes floss thread 320 prior to the thread being reeled in by the unidirectional rotation of the alternative spool enclosing base 258 to promote an encapturing of used floss about annular skirt 259 under flange cap 261 of the spool enclosing base.

As best shown in FIG. 21, the alternative spool enclosing base 258 has a plurality of groove paths 330 forming a groove pattern 332 interconnected with a plurality of notch set points 334 on the top surface 267 of flange cap 261. In the initial threading of floss thread 320, the floss is threaded through any one of the notch set points 334 across groove path 330 to another of the notch set points 334. Once thus threaded groove pattern 332 will serve as floss indexing means assisting the user to replace in a measured manner the operative length of used dental floss with a corresponding length of new floss. In this regard the distance between notch set points 334 of groove pattern 332 corresponds to the distance of operative thread between arms 314 and 316. When alternative spool enclosing base 258 is rotated one of the notch set points 334 will rotate to reference indicia 336. The travel movement of each notch set point 334 to reference indicia 336 during such rotation replaces in a measured manner the operative length of used dental floss reeled in during the rotation with a corresponding length of new dental floss across arms 314 and 316. In this manner the groove pattern 332 operates in conjunction with reference indicia 336 as a floss indexing means such that the advancement of new floss across arms 314 and 316 is in a measured manner to just replace the used floss taken up during the rotation.

The present invention provides a multiple lock central floss holder of two piece construction namely a body and a spool enclosure assembly. The body need not be discarded but can be repeatably used with replacement spool enclosure assemblies containing a spool of dental floss. The relatively simple construction of the multiple lock dental floss holder may be made at minimized cost of plastic resins suitable for injection molding.

It is believed that the MULTIPLE LOCK DENTAL FLOSS HOLDER AND SPOOL ENCLOSURE ASSEMBLY THEREFOR of the present invention in its described embodiments and with its attended advantages will be fully understood from the foregoing description, and that changes may be made in form, construction, and arrangement of the several parts thereof without departing from the spirit or scope of the invention or sacrificing any of the attendant advantages. The preferred embodiments illustrated are not intended to be exhausted or to limit the invention to the precise form disclosed. Accordingly, the scope of the invention is only to be limited as necessitated by the accompanying claims.

I claim:

1. A dental floss holder for receiving a spool of dental floss and dispensing and maintaining a length of said dental floss in a taut condition comprising:
   a pin having a base portion, a neck portion, a stem portion extending from said neck portion, and a distal end;
   a body having a handle portion, an intermediate portion for housing a spool of dental floss, and a forked end portion including two spaced arms, each arm having at least one floss receiving slot at a distal end thereof whereby a taut length of dental floss can be held in said slots across a span between said arms, said intermediate portion having a through bore opening on one side into a spool receiving cavity and on the other side onto an irregular surface;
   a spool enclosing base received in said cavity and having an annular cavity about a seating hub for receiving a spool of dental floss, said hub capable of receiving said pin when said pin is inserted through said through bore of the intermediate portion and into said hub;
   coupling means between said base portion of said pin and said hub permitting selective pressure against a length of floss positioned between said cap and said irregular surface;
   gripping means including said irregular surface for selectively locking in place the length of dental floss positioned between said base portion of said pin and said irregular surface; and
   means for unidirectional dispensing and collecting the dental floss across said arms to prevent release of tension in the dispensed length of dental floss.

2. The dental floss holder according to claim 1 wherein the gripping means comprises said base portion and said neck portion of said pin forming an irregular surface for coupling in a mated engagement with the irregular surface of the intermediate portion, said pin being capable of axial movement to a position of non-mated engagement or to a position of mated engagement of said irregular surfaces to thereby, respectively, selectively allow release or capture of a length of dental floss between the irregular surface of the base portion and neck portion of said pin and the adjacent irregular surface of the intermediate portion.

3. The dental floss holder according to claim 1 wherein the gripping means comprises said neck portion being tapered for coupling in a mating engagement with said through bore of said intermediate portion, said pin being capable of axial movement to a position of non-mated engagement or to a position of mated engagement to thereby, respectively, selectively allow release or capture of a thread of dental floss between said base portion of said pin and said intermediate portion.

4. The dental floss holder according to claim 1 wherein the coupling means between said base portion of said pin and said hub permitting selective pressure against a length of dental floss positioned between said base portion and said irregular surface of the intermediate portion comprises the spool enclosing base and pin being oppositely aligned from the other, said pin being capable of axial movement, by pressure of a finger of a user upon said pin, cooperative with said hub to establish an unlock position or a locked position to thereby apply selective pressure against said length of dental floss.

5. The dental floss holder according to claim 4 wherein said hub further comprises a plurality of legs, each leg having a detent cooperative with a groove or taper on said pin to establish an unlock position or a lock position.

6. The dental floss holder according to claim 1 wherein the means for unidirectional dispensing and collection of floss comprises the spool enclosing base having an annular skirt rearwardly extending from a flange cap, the external surface of which includes a plurality of guide teeth cooperative with a ratcheting mechanism in the side wall of said spool receiving cavity of the intermediate portion to allow rotation of the spool enclosure piece in one direction while preventing rotation in its opposite direction.

7. The dental floss holder according to claim 1 wherein the means for unidirectional dispensing and collection of floss comprises the spool enclosing base having an annular skirt rearwardly extending from a flange cap, the external surface of which includes a plurality of guide teeth cooperative with a plurality of ratcheting mechanisms in the side wall of said spool receiving cavity of the intermediate portion to allow rotation of the spool enclosure piece in one direction while preventing rotation in its opposite direction.

8. The dental floss holder according to claim 1 wherein the means for unidirectional dispensing and collection of floss comprises the spool enclosing base having an annular skirt rearwardly extending from a flange cap, the external surface of which includes a ratcheting mechanism cooperative with a plurality of guide teeth in the side wall of said spool receiving cavity of the intermediate portion to allow rotation of the spool enclosure piece in one direction while preventing rotation in its opposite direction.

9. The dental floss holder according to claim 1 wherein the means for unidirectional dispensing and collection of floss comprises the spool enclosing base having an annular skirt rearwardly extending from a flange cap, the external surface of which includes a plurality of ratcheting mechanisms cooperative with a plurality of guide teeth in the side wall of said spool receiving cavity of the intermediate portion to allow rotation of the spool enclosure piece in one direction while preventing rotation in its opposite direction.

10. The dental floss holder according to claim 1 wherein said forked end portion extends from the body at an oblique angle to the handle.

11. The dental floss holder according to claim 1 wherein the spool enclosing base has a flange cap having a slit therethrough for insertion of a length of dental floss therein.

12. The dental floss holder according to claim 1 wherein the handle portion of the body is of an elongate shape having a hole near its terminal end of sufficient dimension to be hung from a hook.

13. The dental floss holder according to claim 1 wherein said forked end portion is generally U-shaped.

14. The dental floss holder according to claim 1 wherein said intermediate portion or said forked end portion of the body or said two spaced arms thereof contain a groove path for receiving a properly dispensed and orientated length of dental floss.

15. The dental floss holder according to claim 1 wherein said intermediate portion or said forked end portion of the body or said two spaced arms thereof contain indicia for directing a user to properly dispense and orientate a length of dental floss.

16. The dental floss holder according to claim 1 wherein the seating hub comprises a plurality of legs.

17. The dental floss holder according to claim 1 further including floss indexing means on said spool enclosing base and body.

18. The dental floss holder according to claim 17 where said floss indexing means comprise a plurality of grooves and notches on said spool enclosing base and a reference indicia on said body, said grooves and notches capable of receiving a thread of dental floss and forming a groove pattern such that each groove interconnects with a notch to which a knot of said floss thread may be set, the distance between notches corresponding to said span between said two spaced arms, said notches capable of being aligned to said reference indicia during rotation of said spool enclosing base such that rotation of said notches relative to said reference indicia replaces in a measured manner the length of floss in said span between said spaced arms with a corresponding length of new floss.

19. A dental floss holder for receiving a spool of dental floss and dispensing and maintaining a length of said dental floss in a taut condition comprising:

a pin having a base portion, a platform portion, a neck portion, a stem portion extending from said neck portion, and a distal end;

a body having a handle portion, an intermediate portion for housing a spool of dental floss, and a forked end portion including two spaced arms, each arm having at least one floss receiving slot at a distal end thereof whereby a taut length of dental floss can be held in said slots across a span between said arms, said intermediate portion having a through bore opening on one side into a spool receiving cavity and on the other side onto an irregular surface;

a spool enclosing base received in said cavity and having an annular cavity about a seating hub for receiving a spool of dental floss, said hub capable of receiving said pin when said pin is inserted through said through bore of the intermediate portion and into said hub;

coupling means between said base portion of said pin and said hub permitting selective pressure against a length of floss positioned between said cap and said irregular surface;

gripping means including said irregular surface for selectively locking in place the length of dental floss positioned between said base portion of said pin and said irregular surface; and means for unidirectional dispensing and collecting the dental floss across said arms to prevent release of tension in the dispensed length of dental floss.

20. The dental floss holder according to claim 19 wherein the gripping means comprises said base portion, platform portion, and neck portion of said pin forming an irregular surface for coupling in a mated engagement with the irregular surface of the intermediate portion, said pin being capable of axial movement to a position of non-mated engagement or a position of mated engagement of said irregular surfaces to thereby, respectively, selectively allow release or capture of a length of dental floss between the irregular surface of the base portion, platform portion, and neck portion of said pin and the adjacent irregular surface of the intermediate portion.

21. The dental floss holder according to claim 19 wherein the gripping means comprises said neck portion being tapered for coupling in a mating engagement with said through bore of said intermediate portion, said pin being capable of axial movement to a position of non-mated engagement or a position of mated engagement to thereby, respectively, selectively allow release or capture of a length of dental floss between said base portion of said pin and said intermediate portion.

22. A dental floss holder according to claim 19 wherein the coupling means between said base portion of said pin and said hub permitting selective pressure against a length of dental floss positioned between said base portion and said irregular surface of the intermediate portion comprises the spool enclosing base and pin being oppositely aligned from the other, said pin being capable of axial movement, by pressure of a finger of a user upon said pin, cooperative with said hub to establish an unlock position or a locked position to thereby apply selective pressure against said length of dental floss.

23. The dental floss holder according to claim 19 wherein the means for unidirectional dispensing and collection of floss comprises the spool enclosing base having an annular skirt rearwardly extending from a flange cap, the external surface of which includes a plurality of guide teeth cooperative with a ratcheting mechanism in the side wall of said spool receiving cavity of the intermediate portion to allow rotation of the spool enclosure piece in one direction while preventing rotation in its opposite direction.

24. The dental floss holder according to claim 19 wherein the means for unidirectional dispensing and collection of floss comprises the spool enclosing base having an annular skirt rearwardly extending from a flange cap, the external surface of which includes a plurality of guide teeth cooperative with a plurality of ratcheting mechanisms in the side wall of said spool receiving cavity of the intermediate portion to allow rotation of the spool enclosure piece in one direction while preventing rotation in its opposite direction.

25. The dental floss holder according to claim 19 wherein the means for unidirectional dispensing and collection of floss comprises the spool enclosing base having an annular skirt rearwardly extending from a flange cap, the external surface of which includes a ratcheting mechanism cooperative with a plurality of guide teeth in the side wall of said spool receiving cavity of the intermediate portion to allow rotation of the spool enclosure piece in one direction while preventing rotation in its opposite direction.

26. The dental floss holder according to claim 19 wherein the means for unidirectional dispensing and collection of floss comprises the spool enclosing base having an annular skirt rearwardly extending from a flange cap, the external surface of which includes a plurality of ratcheting mechanisms cooperative with a plurality of guide teeth in the side wall of said spool receiving cavity of the intermediate portion to allow rotation of the spool enclosure piece in one direction while preventing rotation in its opposite direction.

27. The dental floss holder according to claim 19 wherein said forked end portion extends from the body at an oblique angle to the handle.

28. The dental floss holder according to claim 19 wherein the spool enclosing base has a flange cap having a slit thereon for insertion of a length of dental floss therein.

29. The dental floss holder according to claim 19 wherein the handle portion of the body is of an elongate shape having a hole near its terminal end of sufficient dimension to be hung from a hook.

30. The dental floss holder according to claim 19 wherein said forked end portion is generally U-shaped.

31. The dental floss holder according to claim 19 wherein said intermediate portion or said forked end portion of the body or said two spaced arms thereof contain a groove path for receiving a properly dispensed and orientated length of dental floss.

32. The dental floss holder according to claim 19 wherein said intermediate portion or said forked end portion of the body or said two spaced arms thereof contain indicia for directing a user to properly dispense and orientate a length of dental floss.

33. The dental floss holder according to claim 19 wherein the seating hub comprises a plurality of legs.

34. A dental floss holder according to claim 19 wherein said hub further comprises a plurality of legs, each leg having a detente cooperative with a groove or taper on said pin to establish an unlock position or a lock position.

35. The dental floss holder according to claim 19 further including floss indexing means on said spool enclosing base and body.

36. The dental floss holder according to claim 35 where said floss indexing means comprise a plurality of grooves and notches on said spool enclosing base and a reference indicia on said body, said grooves and notches capable of receiving a thread of dental floss and forming a groove pattern such that each groove interconnects with a notch to which a knot of said floss thread may be set, the distance between notches corresponding to said span between said two spaced arms, said notches capable of being aligned to said reference indicia during rotation of said spool enclosing base such that rotation of said notches relative to said reference indicia replaces in a measured manner the length of floss in said span between said spaced arms with a corresponding length of new floss.

37. A spool enclosure assembly for use in a dental floss holder having a through bore opening on one side into a spool receiving cavity and on the other side onto an irregular surface comprising: a pin having a base portion, a neck portion, a stem extending from said neck portion, and a distal end;

a spool enclosing base dimensioned to be received in said cavity and having an annular cavity about a seating hub for receiving a spool of dental floss, said hub being capable of receiving said pin when said pin is inserted through said through bore and into said hub, said base portion and neck portion of said pin forming an irregular surface for coupling in a mating engagement with the irregular surface of the dental floss holder, and said pin having a deviation in its outer surface capable of selective connection with said hub and said pin being capable of axial movement with respect to said hub to a position of non-mated engagement or to a position of mated engagement of said irregular surfaces to thereby, respectively, selectively allow release or capture of a length of dental floss between the irregular surface of the base portion and neck portion of said pin and the irregular surface of the dental floss holder.

38. A spool enclosure assembly for use in a dental floss holder having a through bore opening on one side into a spool receiving cavity and on the other side onto an irregular surface comprising: a pin having a base portion, a platform portion, a neck portion, a stem portion extending from said neck portion, and a distal end;

a spool enclosing base dimensioned to be received in said cavity and having an annular cavity about a seating hub for receiving a spool of dental floss, said hub capable of receiving said pin when said pin is inserted through said through bore and into said hub, said base portion, platform portion, and neck portion forming an irregular surface for coupling in a mating engagement with the irregular surface of the dental floss holder, and said pin having a deviation in its outer surface capable of selective connection with said hub and said pin being capable of axial movement with respect to said hub to a position of non-mated engagement or to a position of mated engagement of said irregular surfaces to thereby, respectively, selectively allow release or capture of a length of dental floss between the irregular surface of the base portion, platform portion, and neck portion and the irregular surface of the dental floss holder.

* * * * *